US00PP21363P2

(12) United States Plant Patent
Stahlhut

(10) Patent No.: US PP21,363 P2
(45) Date of Patent: Oct. 5, 2010

(54) CARNATION PLANT NAMED 'CFPC MISO'

(50) Latin Name: *Dianthus caryophyllus*
Varietal Denomination: CFPC Miso

(75) Inventor: Roy Stahlhut, Watsonville, CA (US)

(73) Assignee: California Florida Plant Company, Salinas, CA (US)

( * ) Notice: Subject to any disclaimer, the term of this patent is extended or adjusted under 35 U.S.C. 154(b) by 0 days.

(21) Appl. No.: 12/459,935

(22) Filed: Jul. 9, 2009

(51) Int. Cl.
*A01H 5/00* (2006.01)

(52) U.S. Cl. ..... Plt./273

(58) Field of Classification Search ..... Plt./273
See application file for complete search history.

(56) References Cited

U.S. PATENT DOCUMENTS

| | | | | |
|---|---|---|---|---|
| PP8,419 P | 10/1993 | Jessel | ..... | Plt./70.6 |
| PP9,267 P | 8/1995 | Jessel | ..... | Plt./70.5 |
| PP17,120 P2 | 9/2006 | Hasegawa | ..... | Plt./272 |

*Primary Examiner*—Kent L Bell
(74) *Attorney, Agent, or Firm*—Phase M, LLP

(57) ABSTRACT

A new variety of carnation plant named 'CFPC Miso', having short stature and bright white flowers with a burgundy purple edge.

1 Drawing Sheet

Latin name of the genus and species: Botanical classification: *Dianthus caryophyllus.*

Variety denomination: The new carnation variety denomination is 'CFPC Miso'.

BACKGROUND OF THE INVENTION

The present invention comprises a new and distinct cultivar of hybrid carnation botanically known as *Dianthus caryophyllus*, and referred to by the cultivar name 'CFPC Miso'. The new variety, identified as selection no. 020576, originated from a cross made by Roy Stahlhut in a controlled breeding program in Salinas, Calif. The female parent of the new variety is the variety known as 'CFPC Cotillion' (U.S. Plant Pat. No. 9,267) and the male parent is the variety known as 'CFPC Cupid' (U.S. Plant Pat. No. 8,419). The new variety 'CFPC Miso' has been asexually reproduced by vegetative side shoot cuttings in Salinas, Calif. and the distinguishing characteristics are retained through successive generations of asexual reproduction.

BRIEF SUMMARY OF THE INVENTION

'CFPC Miso' is a potted spray-type carnation plant variety having a very short stature with well presented flowers that have a distinctive broad burgundy purple edge and bright white center.

COMPARISON WITH FEMALE PARENT

Plants of the new carnation variety 'CFPC Miso' are similar to the female parent 'CFPC Cotillion' in plant habit and growth rate. Under similar growing conditions in Salinas, Calif., under commercial practice, plants of the new carnation variety 'CFPC Miso' differed from plants of 'CFPC Cotillion' in the following characteristics:

1. The new variety 'CFPC Miso' produces white flowers with a dark burgundy purple edge whereas 'CFPC Cotillion' produces light pink and picotee wine-red flowers.
2. Plants of the new variety 'CFPC Miso' have shorter stature than plants of 'CFPC Cotillion'.

COMPARISON WITH MALE PARENT

Plants of the new carnation variety 'CFPC Miso' are similar to the male parent 'CFPC Cupid' in plant habit and growth rate. Under similar growing conditions in Salinas, Calif., under commercial practice, plants of the new carnation variety 'CFPC Miso' differed from plants of the male parent 'CFPC Cupid' in the following characteristics:

1. The new variety 'CFPC Miso' produces white flowers with a dark burgundy purple edge whereas 'CFPC Cupid' produces pink flowers.
2. The new variety 'CFPC Miso' has smaller but better formed flowers than 'CFPC Cupid' that do not split their calyx.

COMPARISON WITH OTHER SIMILAR VARIETIES

Plants of the new carnation variety 'CFPC Miso' are similar to plants of the variety 'CFPC Evermore' (U.S. Plant Pat. No. 17,120) in plant habitat and growth rate. Under similar growing conditions, however, in Salinas, Calif., under commercial practice, plants of the new carnation variety 'CFPC Miso' differed from plants of 'CFPC Evermore' in the following characteristics:

1. Plants of the new variety 'CFPC Miso' have shorter stature than plants of 'CFPC Evermore'.
2. Plants of the new variety 'CFPC Miso' have earlier maturity than plants of 'CFPC Evermore'.

BRIEF DESCRIPTION OF ILLUSTRATION

A typical specimen of the plant and flowers for the new carnation variety 'CFPC Miso' is shown in the accompanying photograph. The colors shown are as true as possible within the usual limits of this kind of illustration. FIG. 1 is a whole plant view of the new variety 'CFPC Miso' grown in a pot. The plant shown in the illustration is 119 days from date of planting.

DETAILED BOTANICAL DESCRIPTION

The following description of the new carnation variety 'CFPC Miso' is of plants 119 days from planting grown in a commercial greenhouse in Salinas, Calif. The cultivar has not been observed under all possible environmental conditions. The phenotype may vary significantly with variations in the environment such as temperature, length of day and light intensity without any variance in genotype.

Plants of the new variety have been grown successfully under temperature conditions averaging about 18° C. at night and about 24° C. to 28° C. during the day under light conditions of about 14 hours. Plants are daylight neutral and flower throughout the year. Chemical growth regulators are not required for production. The new variety may be produced as a potted spray-type carnation. To produce a commercial product the plants may be pinched once with the center bud removed. Pinched plants are about 6 inches tall and about 6 inches in diameter. Flower diameter averages about 1½ inches with a crown of about ¾ inch. Foliage is generally about 3½ inches long and about ¼ inch at the widest point. The typical container size for commercial growth is 4½ inches.

It has been observed that the shelf life of the new variety is about 21 days with a time to first bud opening of about 15-16 weeks. The plant hardiness zone has not been determined. The commercial classification of the new carnation variety is a potted spray-type.

The following description is with respect to a plant produced as a potted spray-type carnation. The plant and flower measurements and foliage size are established as an average using standard commercial cultural practices. In the description of this new carnation variety, color values have been taken from The Royal Horticultural Society Colour Chart (R.H.S.C.C.).

PLANT

Height (inches): 6.
Form: Herbaceous.
Growing habit: Semi upright.
Branching characteristics: 3-4 laterals per stem.
Breaking action: 6-8 breaks per plant with strong straight stems.
First appearance of color in buds: 109 days after planting.
Vigor: Excellent.
Shelf life: 21 days.
Blooming habit: Spray type.
Blooming season: Year round.
Lastingness of blooms: About 10 days.
Disease (Susceptibility/Resistance observed): Excellent resistance to soil-borne diseases such as *Fusarium oxysporum* and *F. graminearium*, and root rots such as damping off, water molds and similar types, as are typical of carnations.
Pest susceptibility/resistance: Not evaluated or observed.
Drought and temperature susceptibility/resistance: Not evaluated or observed.
Mutation prone: No.
Propagation:
- *Type.*—Side shoot cuttings.
- *Time to rooting.*—18 days with soil temperatures of about 18° C. to 21° C.
- *Rooting habit.*—Good fibrous system.

Growth treatments or special conditions: Single pinch.

FOLIAGE

Stem:
- *Length (inches).*—4.
- *Diameter (inches).*—⅜ (at base).
- *Texture.*—Smooth.
- *Cross section.*—Edged.
- *Color.*—143C internode. 145D node.

Number of leaves per lateral branch: 14.
Arrangement of leaves: Bi-lateral along the stem.
- *Shape of leaf.*—Long, narrow, lanceolate.
- *Size of leaf width (inches).*—¼ Length (inches): 3½.
- *Leaf apex.*—Acute.
- *Edge.*—Smooth.
- *Base.*—Smooth.
- *Aspect.*—Elliptic.
- *Surface texture.*—Top: smooth. Bottom: smooth.

Leaf venation: Prominent mid-vein at underside.
Leaf longitudinal axis: Recurved.
Leaf cross section (upper side): Weakly concave.
Leaf color: Mature Leaf, upper side: 137A; under side: 137B.
- *Young Leaf, upper side.*—130A; under side: 137A.

Leaf waxy layer: Medium.

FLOWER

Flower appearance: Matte to shiny.
Flower type: Double.
Flower profile of upper part of corolla: Convex.
Flower profile of lower part of corolla: Flat convex.
Flower shape: Somewhat dome shape, rounded.
Number of blossom per branch: 5.
- *Depth of fully expanded blossoms (inches).*—¼.
- *Diameter of fully expanded blossoms (inches).*—1½.

Calyx:
- *Sepals number.*—5.
- *Length (inches).*—¼.
- *Width (inches).*—¼.
- *Color.*—Outer side base: 144B. Outer side middle to tip: 143A. Inner side: 138C.
- *Texture.*—Smooth.
- *Appearance.*—Matte with waxy bloom.
- *Shape.*—Cylindrical.

Flower petals:
- *Form/shape.*—Fan shape.
- *Petal edge.*—Edge type: crenate-dentate Width: 1/16 inch. Depth: 1/16 inches.
- *Texture.*—Smooth.
- *Appearance.*—Matte-shiny.
- *Petal surface of blade.*—Undulating.
- *Number per flower.*—28.
- *Outer petals.*—Length (inches): 1½ Width (inches): ⅞.
- *Inner petals.*—Length (inches): 1⅜ Width (cm): ¾.

Fragrance: Weak perfume.
Flower bud (at onset of color):
- *Length (inches).*—⅞.
- *Diameter (inches).*—5/16.
- *Form/shape.*—Cylindrical.

Flower color:
1. *General tonality.*—White blush burgundy purple.
2. *Petals, upper surface.*—Between 155D and 62D.
3. *Petals, lower surface.*—Whiter than 155D.
4. *Petals, edge.*—185A to 60A.
5. *Petals, center.*—Between 155D and 62D.
6. Early bud:.—185A to 60A.

Color distribution.—Edged-speckled.
Petal macule (random spots): Present.
Flower progression with age: Burgundy purple blush fades slightly, edge does not fade.

REPRODUCTIVE ORGANS

Gynoecium: Pistillate.

*Pistil number.*—1.

*Pistil length* (*inches*).—1½.

*Stigma color.*—White with purple flush.

*Stigma shape.*—Filamentous.

*Style color.*—Whiter than 155D.

*Style length* (*inches*).—1¼.

*Style number.*—Only two.

Ovary:

*Shape.*—Ovoid.

*Surface.*—Smooth.

*Color.*—Base: 145C. Body: 145C. Apex: 144A.

Androecium: None produced.

Fruit and seeds: None produced.

What is claim is:

1. A new and distinct variety of carnation plant, substantially as described and illustrated herein.

* * * * *

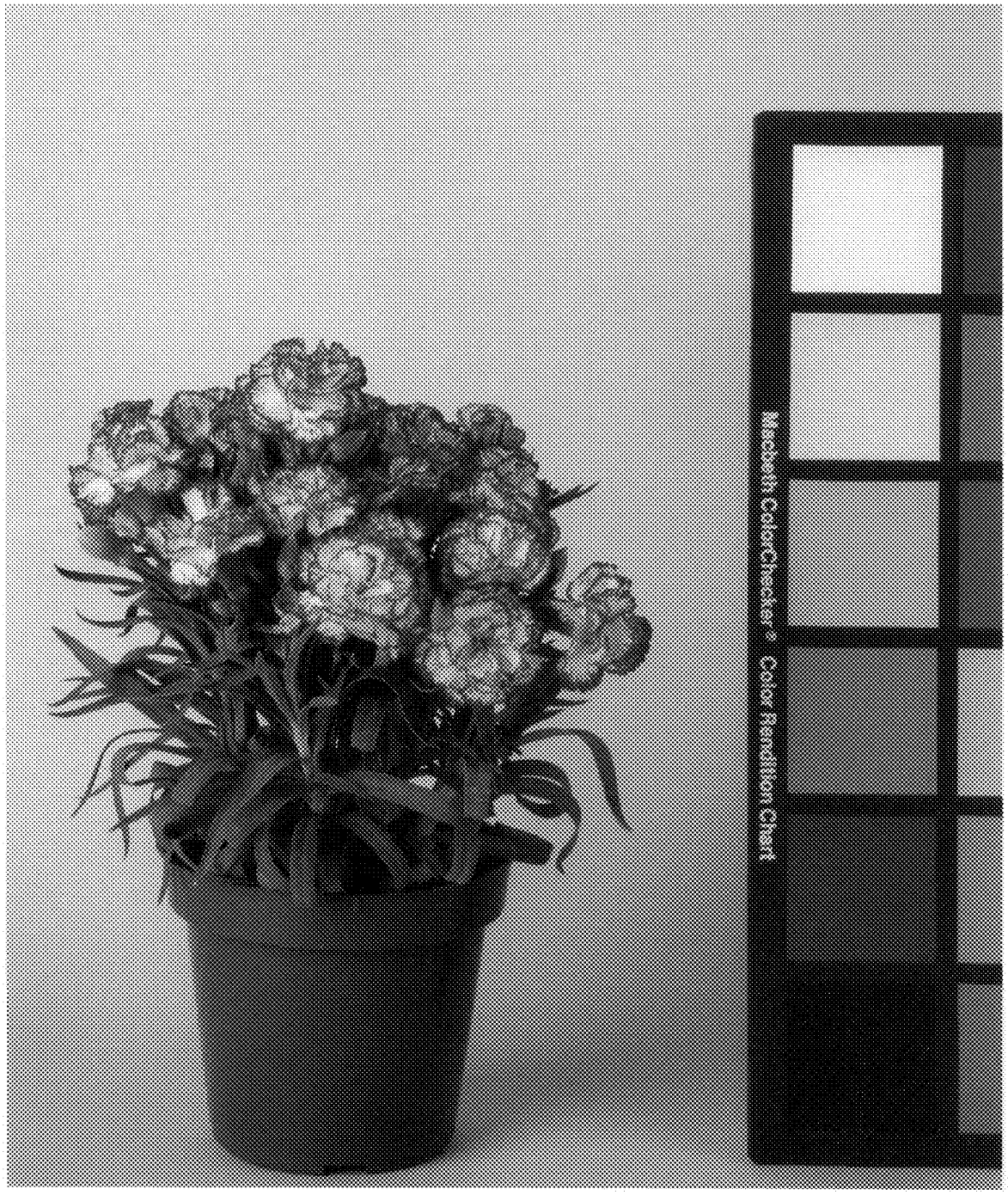
Munsell Color Chart
Color Rendition Chart